United States Patent
Kwiatkowski et al.

[11] Patent Number: 6,127,529
[45] Date of Patent: Oct. 3, 2000

[54] METAL-CHELATING 2,6-DISUBSTITUTED PYRIDINE COMPOUNDS AND THEIR USE

[75] Inventors: Marek Kwiatkowski; Christian Sund; Jyrki Ylikoski; Veli-Matti Mukkala; Ilkka Hemmilä, all of Turku, Finland

[73] Assignee: Wallac Oy, Turku, Finland

[21] Appl. No.: 07/759,437

[22] Filed: Sep. 13, 1991

Related U.S. Application Data

[63] Continuation of application No. 07/535,484, Jun. 11, 1990, abandoned, which is a continuation of application No. 07/212,773, Jun. 29, 1988, abandoned.

[51] Int. Cl.$^7$ ............... C07F 15/00; C07F 9/58; C07C 245/00; C07D 401/06
[52] U.S. Cl. ............... 534/10; 534/560; 546/22; 546/266; 546/267; 546/278.7
[58] Field of Search ............... 534/10, 560; 546/278.7, 546/267, 266, 22

[56] References Cited

U.S. PATENT DOCUMENTS 4,343,935  8/1982  Laidler ............... 546/329

(List continued on next page.)

FOREIGN PATENT DOCUMENTS

| | | |
|---|---|---|
| 0203047 | 11/1986 | European Pat. Off. . |
| 0289939 | 1/1989 | European Pat. Off. ............... 546/2 |
| 2627487 | 8/1989 | France ............... 546/341 |
| 0078663 | 3/1990 | Japan ............... 546/329 |
| WO 87/07955 | of 0000 | WIPO . |
| 88-02784 | 4/1988 | WIPO . |

OTHER PUBLICATIONS

Kwiatkowski et al. Chem. Abstr. vol. 111 Entry 115040 v(1989) Abstracting EP 298939.
Chem. Abstr vol. 113 Entry 112020 q (1990).
Chem. Abstr. vol. 113 Entry 112021 v (1990).

*Primary Examiner*—Alan L. Rotman
*Attorney, Agent, or Firm*—McDermott, Will & Emery

[57] ABSTRACT

Bifuncitonal chelating pyridine compound and its use for conferring chelating properties on organic compounds. The pyridine compound has the structure

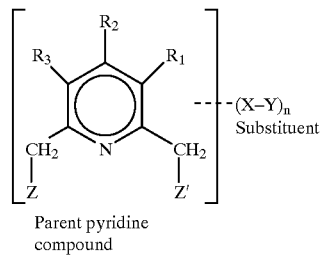

Parent pyridine compound where (i) n is an integer 1 or 2, (ii) $R_1$, $R_2$ and $R_3$ represent groups that have no electrons capable of significantly delocalizing or resonating with the pyridine ring, such as hydrogen, alkyl or aralkyl having an aliphatic carbon atom next to the pyridine ring; at least two of $R_1$, $R_2$ and $R_3$ being hydrogen, iii) Z an Z' represent identical or different structures, each of which comprises at least one heteroatom having a free pair of electrons as that the said at least one heteroatom together with the nitrogen atom of the pyridine ring is capable of chelating a metal ion, iv) - - - - specifies that the group X-Y is a substituent replacing a hydrogen anywhere in the parent pyridine compound, and v) X-Y represents an organic group which is inert to said chelation, and in which iX is an inert and stable bridge and Y is a functional group or a residue of an organic compounbd that has properties conferred on the compound of formula II; said group X-Y being linked to the pyridine ring of formula II via an aliphatic carbon atom attached to and acid ester, salt and chelate forms thereof involving at least one of said chelating heteroatoms.

2 Claims, 1 Drawing Sheet

U.S. PATENT DOCUMENTS

| | | | |
|---|---|---|---|
| 4,374,120 | 2/1983 | Soini | 436/546 |
| 4,590,288 | 5/1986 | Kleman | 546/2 |
| 4,761,481 | 8/1988 | Hale et al. | 546/296 |
| 4,764,613 | 8/1988 | Toth | 546/341 |
| 4,810,782 | 3/1989 | Theodoropulos | 546/2 |
| 4,920,195 | 4/1990 | Kankare et al. | 546/2 |
| 4,950,675 | 8/1990 | Chuchlowski | 546/341 |
| 4,960,895 | 10/1990 | Ohkawa | 546/2 |
| 5,256,535 | 10/1993 | Ylikowski et al. | 435/6 |

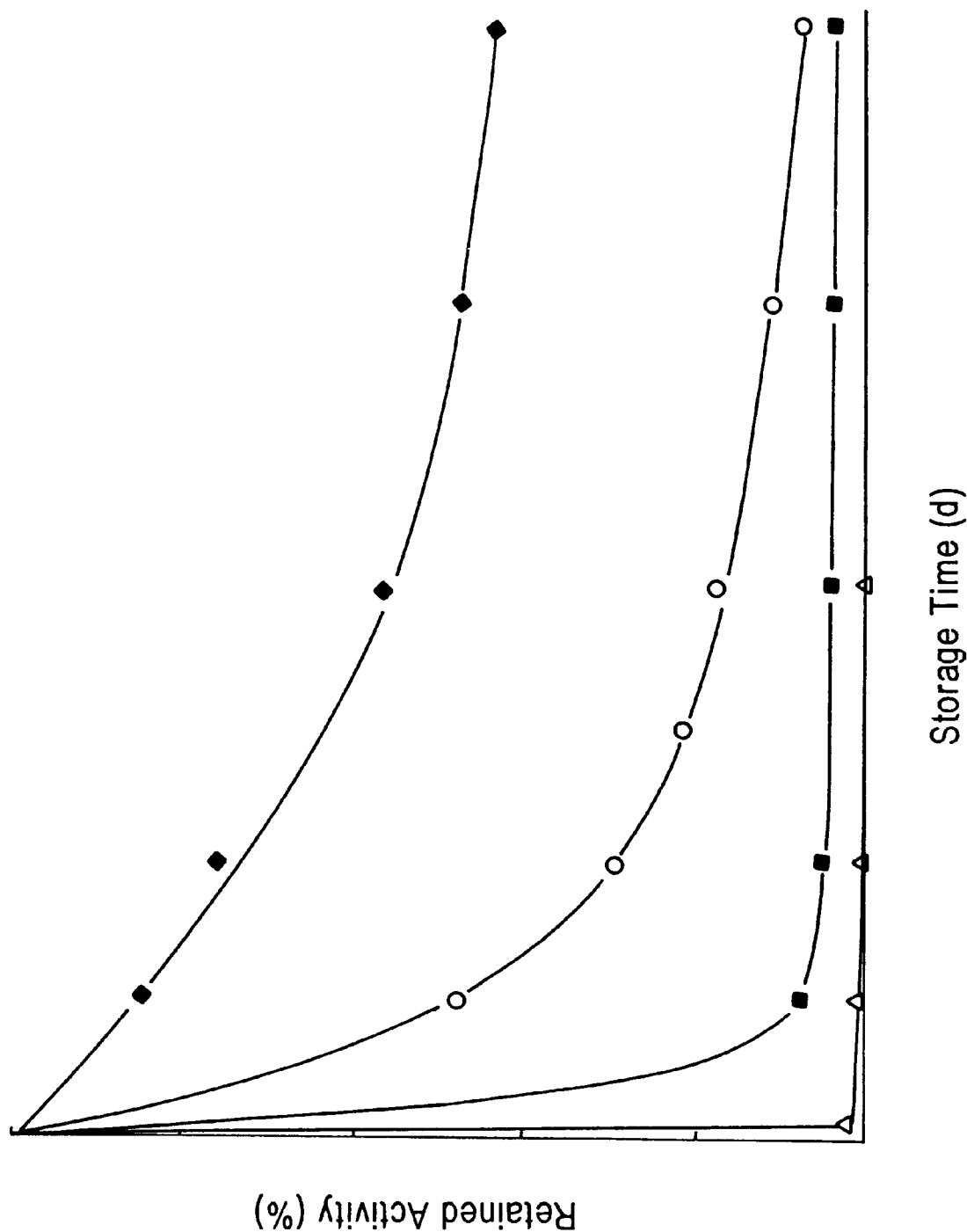

METAL-CHELATING 2,6-DISUBSTITUTED PYRIDINE COMPOUNDS AND THEIR USE

This is a continuation of application Ser. No. 07/535,484, filed Jun. 11, 1990 abandoned which in turn is a continuation of Ser. No. 212,773 filed Jun. 29, 1988 abandoned.

FIELD OF INVENTION

This invention relates to bifuncitonal chelating 2,6-disubstituted pyridine compounds. The compounds are bifunctional in the sense taht a chelating ability is confined to their parent pyridine moiety to which further functions have been added by covalent binding (conjugation) of other organic compounds.

The increased interest in using different metals as labels in various biological systems creates a need for a ligand that binds metals much more strongly than most of the already existing ones. Our invention provides stable metal chelates which may be used as biological markers under conditions that other chelates would not withstand, e.g. elevated temperatures, electrophoretical conditions, presence of additional complexing reagents, or in vivo experiments. This invention also provides a simple method for attaching such chelates to biological samples by means of covalent bonds which are stable under the above conditions and do not alter the complexing properties of the ligand.

DESCRIPTION OF PRIOR ART AND OF THE STRATEGY UTILIZED FOR MAKING THE INVENTION

The discovery of EDTA initiated a series of studies which resulted in the systhesis of ligands of varying metal chelating properties. In the past few years these studies have been extended to the development of several bifuncitonal chelating agents possessing both a chelating roup and a reactive funcitonal group that may react with certain biological molecules.

Labels of this type are already being used in several fields of nuclear medicine. Certain classes of functionalized chelates, especially those which comprise europium or terblun, have bene extensively used as markets in immunoassays or hybridization detection of viral DNA. SOme chelates may be useful reagents in nucleic acid sequencing, DNA or protein fingerprinting and also in fluorescence microscopy. This, of course, mans that the market has to have a high degree of physiochemical stability, inasmuch as it must remain stable not only in diluted physiological systems but also in rather exacting donditions of heat and electric current. Moreover, markers are expected to be stable even in the presence of a great excess of another complexing agent, e.g. EDTA. Many of the ligands existing today do not fulfill these criteria. Generally, derivatives of ethylenediaminetetraacetic acid-EDTA have been considered to belong to this category. Such derivatives lose metal ($Eu^{3+}$) upon boiling at 100° C. for 5 min—typical denaturing conditions of DNA hybridization probes—and are not stable enough under electrophoretical conditions. On the other hand many effectively chelating homobifuncitonal ligands e.g. DTPA (introduced in the form of DTPA dianhydride) lose part of their metal binding capacity as one of the carboxyl groups in involved in the coupling reaction. Additionally, this ligand, when used for labeling in its active form of dianhydride, always crates substantial amounts of crosslinked products, which, together with subsequent difficulties of introducing a metal ion into such a polyligand without causing extensive precipitation, makes this ligand useless for most of the prepartions.

We therefore set out to find a chemically modified ligand that would react rapidly and efficiently with a substrate and would yet retain the metal under the above drastic conditions. In our search for an appropriate stable bifunctional ligand, we focused our attention on ligands of the formula:

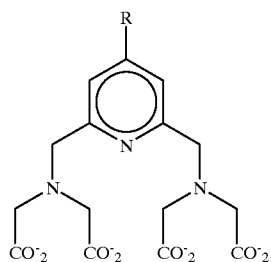

I

Lanthanide chelates of these ligands are known and have been condisered to be very stable in dilute aqueous solutions. It is also known that the substituent R may affect the chelating properties of such a ligand; particulary, substituents of the electron dontating type may greatly decrease the stability of the chelate (Chem.Ber. 117, 948–954 (1984)). The same is probably true even when such a substituent donates electrons via a conjugated system. This conclusion is based on spectral data and on the fact that some functional groups conjugated to a pyridine ring differ markedly in reactivity e.g. amino or isothiocyano as compared to their normal reactivity. nevertheless, compounds having strong electron donating substituents bound to a phenyl ring conjugated to the pyridine nucleus have been presented in EP-A-195,413 and EP-A-203,047 and claimed to be useful for bestowing chelating properties on biologically active molecules.

We achieved our goal by recognizing that a functional group of the type bestowing a covalent binding ability on other organic compounds should be linked to the pyridine ring via an inert bridge having an aliphatic carbon next to the ring, and not as in the prior art via pi-electron systems or strongly electron donating groups directly conjugated to the ring. Synthetically, this introduction of a structure containing the funcitonal group was achieved by derivatization in two different ways—i) at position 4 of the pyridine ring or ii) in the substituents at the 2- and/or 6-positions.

We felt that all the synthetic routes available from the literature and resulting compounds of formula I were rather too complicated. We therefore investigated alternative ways.

We found that 2,4,6-trimethylpyridine (collidine) (1) can be selectively alkylated at the 4-methyl position with a broad range of alkylating reagents yielding products which offer a spectrum of further syntetic alternatives. See Scheme 1.

We found an efficient method for introducing chelating groups e.g. iminobiscarbothoxymethyl groups into the respective pyridine derivative, specifically at the 2 and 6 positions with no effect on the methylene group in the 6 position. Applicaiton of known methods permits the introduction of other than carboxyl groups into the chelating center. Phosphonates can be introduced according to J. Org. Chem. 31, 1603 (1966) and phosphates accordign to a general method presented for instance in Helv. Chim. Acta 70, 173 (1987). A whole range of metallic elements can be ocmplexed with such ligands. Nucl. Med. Biol. 13, 311 (1986) and reference cited therein given an overview of the metals and the preparation technique for chelate formation. We also found an independent method utilizing certain amino acids for introducing reactive groups into the chelate; this is illustrated in Scheme 2.

While the use of α-aminoacids as starting material for the synthesis of chelates is not a novel idea (Brit. Patent 723,316), as far as we know, lysine or other α, ω diamino acids have never been used for such purposes probably because of synthetic difficulties in the selective handling of these molecules.

DESCRIPTION OF THE INVENTION

The compounds of the invention have the common structure given in formula II and comprise also ordinary analogues thereof, such as acid, ester, salt and chelate forms involving one or more of the chelating heteroatoms. The characteristic feature of the compounds is that the group X-Y is linked to the pyridine ring of formula II via an aliphatic carbon atom attached to said ring.

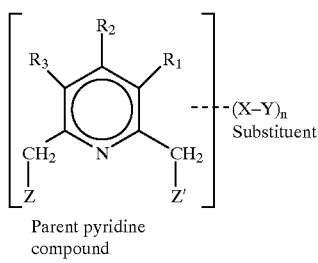

Parent pyridine compound

In formula II, n is an integer 1 or 2, and - - - - - - specifies that the group X-Y is a substituent replacing a hydrogen in the parent pyridine compound.

$R_1$, $R_2$ and $R_3$ are groups having no electron pair that is able to significantly delocalize and resonate with the pyridine ring. They may be selected from hydrogen, alkyl and aralkyl having an aliphatic carbon atom next to the pyrindine ring. At least two of $R_1$, $R_2$ and $R_3$ are hydrogen atoms. The groups may contain from 0–12 carbon atoms and may be exemplified by structures such as straight, branched and cyclic aliphatic hydrocarbon chains, and groups including lower alkyl ($C_1$–$C_5$) and aromatic structures such as phenyl, naphthyl, quinolyl, pyridyl or bipyridyl.

Z and Z' represent identical or different chelating structures, each of which comprises at least one, preferably more than two or three, heteroatoms having a free pair of leectrons and so positioned that the heteroatoms together with the nigrogen atom of the pyridine ring are capable of chelating metal ion. Examples of efficient chelating heteroatoms are amino nitrogen atoms (primary, secondary and tertiary amines), negatively charged oxygen atoms, e.g. in carboxylate anions ($COO^-$), enolate anions ($C=C-O^-$) phosphates or phosphonates. Another good chelating structure is the hydroxamate gorup (CONOH). Efficient chelating also puts certain steric requirements on the bridge linking two chelating heteroatoms together, so that they should be placed at a distance of two atoms from each other, but a three atoms distance may be acceptable. In most cases the bridge contains 1, 2 or 3 aliphatic carbon atoms. Among particularly important Z and Z' structures may be mentioned N-biscarboxymethyl $^{amino}$ and N-bicarboxyethyl $^{amino}$ groups together wit the analogous phosphate ($-N(-CH_2-O-PO_3{}^{2-})_2$) and the phosphonates ($-N(-CH_2-PO_3{}^{2-})_2$). The chelating heteroatoms (N and O) may exist as the corresponding protonated forms and in the case of O also as ester forms such as lower alkyl ($C_1$–$C_6$) or benzyl esters.

X-Y represents an inert organic group in which X is an inert and stable bridge and Y is (a) a functional group or (b) a residue of an organic compound (Y') that has properties retained in the compound of formula II after X-Y has been coupled covalently to the parent chelating pyridine compound. The term "inert" above means that the group or bridge characterized by this adjective does not have any efficient chelating heteroatom closer than at a distance of four atoms from the heteroatoms participating in the chelation of a metal ion. In actual practice this means that the four atoms are normally represented by a four-carbon chain. By "stable" is meant that the bridge X does not deteriorate when the compounds of the invention are used, for instance the bridge does not easily undergo hydrolysis. In formula II, X-Y exists preferably as a substituent replacing a hydrogen in the Z and/or Z' groups or replacing $R_1$, $R_2$ or $R_3$, preferably $R_2$.

Except for the requirement that the bridge X must have an aliphatic carbon, preferably a methylene gorup ($-CH_2-$) at its left end, when attached directly to the pyridine ring, X may also contain at least one structural element selected from among the following: $-NR-$ (secondary and tertiary amine), $-CONR-$ and $-NRCO-$ (substituted amide), $-S-S-$ (aliphatic disulfide), $-S-$ (aliphatic thioether), $-O-$ (ether), $-COO-$ and $-OOC-$ (ester), $-N-N-$ (diaza) and pure hydrocarbon chain which may be straight, branched or cyclic and contain from 1 to 12 carbon atoms. The carbon chain may be purely aliphatic or purely aromatic (including phenyl, naphthyl, quinolyl, pyridyl and bipyridyl), but it may also exhibit both types of structures, such as in alkylaryl, and other inert functional groups not participating in the chelation mentioned above. The symbol R in the substituted amide above represents preferably hydrogen but may be alkyl, for instance an alkyl having less than 5 carbon atoms.

Y may be selected from two main categories (A and B below):

A) Y may be the residue of an organic compound (Y') having certain properties which are substantially retained in the compound of formula II. The compound (Y') may be a biologically active molecule having the ability to participate in biospecific affinity reactions, such as between antigens (heptens) and the homologous antibody active components, complementary nucleic acids, lectins and carbohydrate structures, protein A and IgG etc. This type of biologically active molecules are often called targeting substances (targeting molecules). Usually they have been or can be easily derivatized to contain functional groups permitting conjugation to diversified types of compounds. The compound (Y') may also be a multifunctional organic compound which is bound by one of its functional groups to the bridge X so as to leave at least one of its remaining functional groups free for further derivatization.

B) Y may be a functional group so selected that it can be made to react chemically with a funcitonal group A of an organic compound (Y') so as to form a covalent linkage betwen Y' and a compound of formula II. The selection of Y depends on A and vice versa, but it is believed that any artisan can make the proper selection of mutually reactive groups. Y and A may be selected from among electrophilic and nucleophilic groups. If they are a pair of electrophilic groups or a pair of nucleophilic groups, it is possible for instance to (a) employ oixdative coupling for forming the bond (e.g. $-SH+HS- \rightarrow -S-S-$) or (b) convert one of the groups of the pair chemically to a group of the opposite type. An example of the latter case is the activation with bifunctional coupling reagents (also called activation reagents). If Y is nucleophilic and A electrophilic or vice verse these two groups can usually be reacted with each other without any preceding activation. Most nucleophilic groups comprise a heteroatom having an electron pair available for reaction with an electron deficient atom (electrophilic group).

Examples of suitable funcitonal groups include isothiocyanato, bromoacetamido, iodoacetamido, succinamido, pyridyldithio, mercapto, carboxyl and its active esters (e.g. N-hydroxysuccinimido or p-nitrophenyl), hydroxyl, aldehyde, amino, diazonium, tosyl, mesytylyl, trexyl, phosphodiester or phosphotriester. Other functional groups are known to those skilled in the art.

The reactive group Y does not necessarily have to coexist with the rest of the molecule being in the form of an already existing chelate. For some purposes the chelating part of the molecule may be temporarily protected e.g. in the form of an ester so that the protected ligand will be coupled to the target molecule, and after deblocking may finally form the desired labeled product. The protective group is chosen in accordance with known principles (see for instance Protective Groups in Organic Synthesis; Greene Tenn.; John Wiley & Sons Inc. USA (1981). Factors to be taken into account when the group is chosen are inter alia the stability of the compound with which Y is to be reacted, the reactivity of Y and the type of structure formed upon reaction of Y and the compound intended.

One aspect of the invention comprises the use of a compound of formula II for binding a chelating 2,6-disubstituted pyridine covalently to an organic compound (Y') containing at least one functional group A reactive with Y This aspect of the invention is characterized in that a compound of formula II or an acid, ester, salt or chelate form thereof as previously set forth is contacted with said compound Y so that A and Y react with each other to covalently bind compound Y' and said 2,6-disubstituted pyridine together. After reaction, said acid, ester or salt forms are optionally converted in a manner known per se to the required chelate form. The reaction conditions required for the binding depend on the pair of fucntional groups (Y and A), Y', and the compound of formula II employed etc. and are known per se. In this aspect of the invention the acid, ester, salt and chelate forms, n, $R_1$, $R_2$, $R_3$, Z, Z', Y, X and - - - - - have the same meanings as set forth above except that Y is only a functional group.

Protective groups known per se are sometimes required in order to perform the binding. See the above mentioned text-book.

The preferred compounds of the invention have been summarized in formula III.

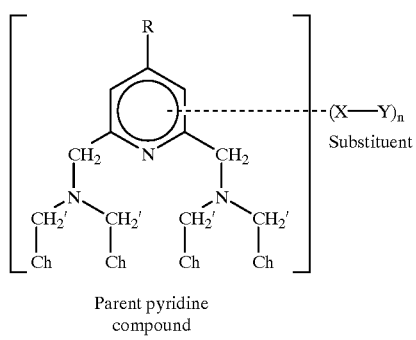

Parent pyridine compound

In formula III $R_2$, X and Y have the same meaning as previously stated. - - - - means that X-Y is a substituent replacing either $R_2$ or H', and n is an integer 1 or 2, with the proviso that n is always 1 when X-Y is a substituent replacing $R_2$. Ch is a chelating group selected from —COO$^-$, —OPO$_3^{2-}$ and —PO$_3^{2-}$. This preferred aspectof the invention also comprises the acid, ester, salt and chelate forms as defined above.

The following examples are presented to illustrate the present invention. In all example, the commericla chemicals used were of the highest, preferably analystical quality, and the remaining reagents were prepared using conventional procedures. Most of the solvents were routinely distilled. Pyridine, acetonitrile and tetrahydrofuran were dried by refluxing them with calcium hydride prior to the distillation. Support for short column chromatography (flash chromatography) Kieselgel G60, and TLC Plates Kieselgel 60F-254 were obtained from Merck. NMR spectra were recorded using either a Jeol JNM CX400 or Hitachi Perkin-Elmer R600 spectrometer and using TMS as the internal standard. UV spectra were recorded on a Bechman DU-8 Spectrophotometer, and IR spectra were recorded using a Bechman IR-8 spectrophotometer. Spectra of the individual compounds synthesized were recorded and were consistent with the structures given.

The analytical TLC plates were developed in several systems listed here:

| System A | MeOH/CHCl$_3$ | 1:9 |
|----------|---------------|-----|
| System B | MeOH/CHCl$_3$ | 1:4 |
| System C | MeOH/CHCl$_3$ | 1:19 |
| System D | MeOH/CHCl$_3$ | 3:7 |
| System F | 1M NH$_4$Ac/EtOH | 2:8 |

Examples 1–12 see reaqction scheme 3. Examples 13–23 see reaction scheme 4.
Examples 24–33 see reaction scheme 5. Examples 34–42 see reaction scheme 6.
Exampels 43–45 see reaction scheme 7. Examples 46–49 see reaction scheme 8.

All numbered structures presented in the schemes correspond to synthesized compounds. Explanations of the abbreviations are given in the examples. All synthesized compounds are presented by chemical formula and name. In case of any discrepancy between the formula and the name, the former is always valid.

EXAMPLE 1

2,6-Dimethyl-4-(2-phenylethyl)pyridine (2)

Liquid ammonia (150 ml) was introduced into a 250 ml three-necked round bottomed flask equipped with a mechanical stirrer, dropping funnel and outlet tube and immersed in a dry ice/ethanol bath. Sodium amide was generated by addition of 20 mg of iron nitrate (Fe$^{3+}$) followed by metallic sodium (2.09 g, 0.09 mol). The deep blue solution was stirred for one hour and a solution of collidine (1) (10.06 g, 0.083 mol) in 20 ml of dry diethylether was introduced into the reaction by addition over a period of 15 min. The resultant yellow suspension was stirred for an additional 45 min, followed by the addition or benzylchloride (6.33 g, 0.05 mol) dissolvedin 10 ml of dry diethylether. The reaction mixture was stirred for 45 min and excess sodium amide was neutralized by addition of ammonium chloride (4.82 g, 0.09 mol) dissolved in 20 ml of H$_2$O. Ammonia was evaporated and the residue was partitioned between water and diethylether. The collected etheral phase was dried over sodium sulfate and evaporated. The brown residual oil was fractionated, and a fraction distilling at 130° C./0.1 mmHg was colelcted.

Yield=6.17 g (55%), oil, Rf=0.57 (System A)
H$^1$NMR (60 MHz, CDCl$_3$): 7.30–7.05 (m, 7H), 2.90–2.70 (m, 4H), 2.46 (s, 6H)

EXAMPLE 2

2,6-Dimethyl-4-(2-(4-nitrophenyl)ethyl) pyridine (3)

Compound (2) (20 g, 88.9 mmols) was dissolved in THF (150 ml), and nitric acid (6.7 ml, 60% aq. solution, 1 eq) was added. Diethylether was added to the clear solution until it remained turbid, and the mixture was left in the freezer for crystallization. The white crystals of nitrate (quantit. yield) were added in small portions to well-chilled sulfuric acid (150 ml), never allowing the temperature to reach 10° C., whereafter the mixture was warmed at 50° C. for 10 min. The resulting brown solution was poured onto ice and neutralized with solid sodium hydrogen carbonate. The organic material was extracted with chloroform (3×200 ml), and after drying over sodium sulphate, the chloroform extract was flash chromatographed using 4% ethanol/chloroform as a solvent. The appropriate fractions were collected and evaporated yielding a pure yellow solid
Yield 22.82 g (95%) Rf=0.62 (System A)
H$^1$NMR (400 MHz, CDCl$_3$): 8.14 (d, 2H, J=8.7 Hz), 7.30 (d, 2H, J=8.7 Hz), 6.75 (s, 2H), 3.05–2.98 (m, 2H), 2.90–2.84 (m, 2H), 2.48 (s, 6H)

EXAMPLE 3

2,6-Dimethyl-4-(2-(4 nitrophenyl)ethyl) pyridine N-oxide (4)

Compound (3) (22.82 g, 84.5 mmol) was dissolved in chloroform (100 ml), and 16 g (94 mmol) of m-chloroperbenzoic acid (mCPBA) was addedin small portions at RT over a period of 30 min. The mixture was stirred for an additional 2 h and after a negative TLC test for the starting material it was worked up by partitioning between sat. sodium hydrogen carbonate and chloroform. The combined chloroform extracts (3×200 ml) were evaporated yielding a light yellow solid material that was TLC pure.
Yield: 24.55 g (100%) Rf=0.40 (System A)
H$^1$NMR (400 MHz, CDCl$_3$): 8.14 (d, 2H, J=8.7 Hz), 7.29 (d, 2H, J=8.7 Hz) 6.93 (s, 2H), 3.06–3.00 (m, 2H), 2.92–2.86 (m, 2H), 2.50 (s, 6H)

EXAMPLE 4

2-Acetoxymethyl-4-(2-(4-nitrophenyl)ethyl)-6-methylpyridine (5)

Compound (4) (24.0 g) was suspended in 100 ml of pentic anhydride. The mixture was refluxed for 20 min which resultedin a homogenous dark solution. Acetic anhydride was evaporated on a Rotavapor and the oily residue was neutralized with saturated sodium hydrogen carbonate, followed by extraction with chloroform (3×200 ml). The chloroform phase was evaporated and the crude material was flashed chromatographed using 2% ethanol/chloroform as a solvent. The pure fractions were evaporated yielding oil that use TLC and WHR pure.
Yield: 19.55 g (69%) Rf=0.71 (System A) H$^1$NMR (400 MHz, CDCl$_3$): 8.14 (d, 2H, J=8.7 Hz), 7.31 (d, 2H, J=8.7 Hz) 6.95 (s, 1H), 6.91 (s, 1H), 5.14 (s, 2H), 3.08–3.92 (m, 2H), 2.97–2.91 (m, 2H), 2.53 (s, 3H), 2.14 (s, 3H)

EXAMPLE 5

2-Acetoxymethyl-4-(2-(4-nitrophenyl)ethyl)-6-methylpyridine N-oxide (6)

Compound (5) (19 g, 60.5 mmol), was oxidized as described in Example 3. The crude, single spot on the TLC product was isolated after standardw work up.

Yield: 18.97 g (95%), oil Rf=0.45 (System A) H$^1$NMR (400 MHz, CDCl$_3$): 8.17 (d, 2H, J=8.8 Hz), 7.32 (d, 2H, J=8.8 Hz) 7.03 (s, 1H), 7.01 (s, 1H), 5.38 (s, 2H), 3.10–3.03 (m, 2H), 3.00–2.93 (m, 2H), 2.52 (s, 3H), 2.20 (s, 3H)

EXAMPLE 6

2,6-Bisacetoxymethyl-4-(2-(4-nitrophenyl)ethyl) pyridine (7)

Compound (6) (18.5 g, 56 mmol), was converted to product (7) in a synthesis analogue to the synthesis in Example 4. The neutralized, end-extracted product was evaporated and flash chromatographed using 2% ethanol/chloroform as a solvent. The pure fractions containing the product were combined and evaporated.

Yield: 12.04 g (61%), oil Rf=0.72 (System A) H$^1$NMR (400 MHz, CDCl$_3$): 8.14 (d, 2H, J=8.8 Hz), 7.31 (d, 2H, J=8.8 Hz), 7.07 (s, 2H), 5.18 (s, 4H), 3.10–2.80 (m, 4H), 2.15 (s, 6H)

EXAMPLE 7

2,6-Bishydroxymethyl-4-(2-(4-nitrophenyl)ethyl) pyridine (8)

Diacetate (7) (12.0 g, 34.1 mmol), was dissolved in 50 ml of ethanol. To this solution stirred at RT, sodium hydroxide 5 H, 20 ml was added at once. After 10 min, when the TLC test for the substrate was negative, the mixture was neutralized with citric acid, and partitioned between sat. sodium hydrogen carbonate and ethanol/chloroform 1:1. The extraction was repeated three times using 100 ml of organic solvent for each extraction. The combined extracts were evaporated and the residual mixture was flash chromatographed using finally 8% ethanol/ chloroform as a solvent. The appropriate pure fractions were collected and evaporated.

Yield: 4.75 g (32%), yellow solid Rf=0.35 (System B) H$^1$NMR (400 MHz, DMSO-d$_6$): 8.15 (d, 2H, J=8.5 Hz), 7.55 (d, 2H, J=8.5 Hz), 7.22 (s, 2H), 5.33 (t, 2H, exchangeable, J=5.5 Hz), 4.48 (d, 4H, J=5.5 Hz) 3.10–3.02 (m, 2H), 3.00–2.94 (m, 2H)

EXAMPLE 8

2,6-Bisbromomethyl-4-(2-(4-nitrophenyl)ethyl) pyridine (9)

To the dihydroxy compound (8) (2.7 g, 9.44 mmol), in 35 ml of dry dichloromethane, phosphorus tribromide (3.63 g, 1.26 ml, 13.41 mmol) was added and the mixture was refluxed for 15 min. The reaction mixture was neutralized with saturated sodium hydrogen carbonate and extracted with chloroform (3×50 ml). The combined extracts were concentrated and crystallized from ethyl acetate.

Yield: 3.91 g (84%)—white crystals Rf=0.73 (System C) H$^1$NMR (400 MHz, CDCld$_3$): 8.15 (d, 2H, J=8.5 Hz), 7.28 (d, 2H, J=8.5 Hz) 7.14 (s, 2H), 4.49 (s, 4H), 3.05–3.02 (m, 2H), 3.01–2.37 (m, 2H)

EXAMPLE 9

2,6-Bis(N,N-bis(ethoxycarbonylmethyl) aminomethyl)-4-(2- (4-nitrophenyl)ethyl pyridine (10)

Compound (9) (3.27 g, 7.9 mmol) and iminodiacetic acid diethylester (5.78 g, 30.5 mmol), were coevaporated together with toluene and redissolved in dry acetonitrile (50 ml). Solid sodium carbonate (10 g) was added and the mixture was refluxed for 2 h, whereupon the salts were filtered out and the filtrate was evaporated. The residue was flash chromatographed and the fractions containing the product evaporated to dryness. To obtain material free from any co-chromatographed iminodiacetic acid diethylester, the oily product was triturated with petrol ether (3×20 ml) which yielded material free from any contaminations.

Yield: 5.09 g (80%), oil Rf=0.27 (System C) H$^1$NMR (400 MHz, CDCl$_3$): 8.08 (d, 2H, J=8.8 Hz) 7.29 (s, 2H), 7.27 (d, 2H, J=8.08 Hz) 4.13 (q, 8H), 3.95 (s 4H), 3.53 (m, 8H), 3.04–2.90 (m, 4H), 1.23 (t, 12H)

EXAMPLE 10

2,6-Bis (N,N-bis(ethoxycarbonylmethyl) aminomethyl)-4-(2- (4-aminophenyl)ethyl pyridine (11)

To the solution of compound (10) (4.8 g, 7.5 mmol) in 50 ml of ethanol, 10% palladium on carbon (100 mg) was added followed by sodium borohydride (378 mg, 10 mmol). The reaction mixture was stirred at RT for 5 min and partitioned between sat. sodium hydrogen carbonate and chloroform. The chloroform extracts (3×50 ml) were concentrated and flash chromatographed to give compound (11) as an oil after evaporation.

Yield: 3.89 g (85%) Pf=0.37 (System A) H$^1$NMR (400 MHz, CDCl$_3$): 7.28 (s, 2H), 6.93 (d, 2,H J=7.3 Hz), 6.60 (d, 2H, J=7.3 Hz), 4.17 (q, 8H), 4.00 (s 4H), 3.59 (s, 8H), 2.87–2.79 (m, 4H), 1.27 (t, 12H)

EXAMPLE 11

2,6-Bis (N,N-bis(carboxymethyl)aminomethyl)-4- (2- (4-aminophenyl) pyridine and its europium (12)

Compound (11) (250 mg) in 20 ml of ethanol, was treated with 1 M sodium hydroxide (10 ml) at RT for 3 h. The pure on TLC product (solvent system acetonitrile/water 4:1) was neutralized with 1 M hydrochloric acid and concentrated. To the residue dissolved in water (25 ml), europium chloride hexahydrate (60 mg dissloved in 5 ml of water was added and the mixture was stirred for 30 min. The excess of europium salt was removed by raising the pH to 8.5 with saturated sodium carbonate solution and filtration of the precipitate. The clear solution was evaporated almost to dryness and (12) was precipitated by addition of 100 ml of acetone. The product was washed on the filter with acetone and dried.

EXAMPLE 12

Europium chelate of 2,6-Bis (N,N-bis (carboxymethyl)aminomethyl)-4-(2- (4-isothiocyanstophenyl)ethyl) pyridine (13)

To the amin chelate (12) (100 mg) dissloved in 5 ml of water and vigorously stirred, thiophosgene (80 μl) dissloved in 3 ml of chloroform was added all at once and the mixture was stirred at RT for 1 h.

The water phase was separated, extracted with chloroform (3×3 ml) and concentrated to a volume of 0.5 ml. Addition of ethanol (10 ml) precipitated (13 ) quantitatively as a white solid. TLC (System Acetonitrile/H$_2$O 4:1) and fluorescence developing with acetonyl acetone/EtOH (1:20) showed only a single product which was negative to a fluorescamine test for free amines.

IR (in KBr): 2100 cm$^{-1}$

EXAMPLE 13

4-(Bromoheptyl)-2,6-dimethyl pyridine (14)

Sodium amide was formed from sodium (1.0 g, 43.5 mmol) in liquid ammonia (100 ml) according to Example 1. Collidine (1) (5.0 g, 41.3 mmol) dissolved in tetrahydrofuran (5 ml) was added dropwise and after 45 min a well-cooled solution of dibromohexane (51.2 g, 210 mmol) in THF (100 ml) was added quickly. The reaction mixture was stirred for 1 h at −40° C. and then left stirring overnight during which times ammonia evaporated.

The residual THF solution was evaporated and the residue was partitioned between water and diethylether. The etheral phase was treated with hydrochloric acid solution (2.0 M, 200 ml), and the pyridinium salts extracted into the aqueous phase were liberated on addition of sodium hydroxide (5 M) to obtain a slightly alkaline solution. The oily products formed were reextracted and separated by silica gel column chromatography.

Yield: 3.54 g (30%) oil Rf=0.48 (System C) H$^1$NMR (60 MHz, CDCl$_3$): 6.73 (s, 2H), 3.37 (t, 2H J=8.5 Hz), 2.44 (s, 6H), 1.70 (t, 2H), 1.30–1.60 (m, 10H).

As a by-product 1,7-Bis(4-(2,6-dimthylpyridyl)heptane (15) was isolated from the same reaction mixture in a 35% yield. H$^1$NMR (400 MHz, CDCl$_3$): 6.77 (s, 4H), 2.48 (s, 12H), 1.58 (t, 4H, J=7.0 Hz), 1.30 (s, 12H).

EXAMPLE 14

4-(7-Phthalimidoheptyl)-2,6-dimethylpyridine (16)

A mixture of compound (14) (3.54 g, 12.5 mmol), potassium phthalimide (2.54 g, 13.7 mmol) and dimethylformamide (25 ml) was heated at 125° C. for 6 h. DMF was evaporated and the residue coevaporated twice with n-butanol and twice with toluene. The dry crude product was purified by flash chromatography. Yield: 3.54 g (81%) viscous oil Rf=0.46 (System A) H$^1$NMR (60 MHz, CDCl$_3$): 7.60–7.95 (m, 4H), 6.76 (s, 2H), 3.68 (t, 2H, J=7 Hz), 2.48 (s, 6H), 2.36–2.60 (m, 2H), 1.23–1.77 (m, 10H)

EXAMPLES 15–21

From 4-(7-Phthalimidoheptyl)-2,6-dimethylpyridine N-oxide (17) to 4-(7-phthalimidoheptyl)-2,6-bis(N, N-bis(ethoxycarbonylmethyl)aminomethyl) pyridine (23). Compounds 17–23 in Scheme 4

These compounds were prepared following the conditions from Examples 3, 4, 5, 6, 7, 8 and 9 respectively. Therefore, only final results will be presented here.

EXAMPLE 15

4-(7-Phthalimidoheptyl)-2,6-dimethylpyridine-N-oxide (17)

Yield: 95% oil Rf=0.38 (System A) H$^1$NMR (60 MHz, CDCl$_3$): 7.60–7.95 (m, 4H), 6.97 (s, 2H), 3.68 (t, 2H J=7 Hz), 2.5 (s, 6H), 2.36–2.60 (m, 2H), 1.23–1.77 (m, 10H).

EXAMPLE 16

2-Acetpxymethyl-4-(7-phthalimidoheptyl)-6-methylpyridine (18)

Yield: 89% oil Rf=0.70 (System A) H$^1$NMR (60 MHz, CDCl$_3$): 7.60, 7.95 (m, 4H), 6.96 (s, 1H), 6.92 (s, 1H) 5.14 (s, 2H), 3.69 (t, 2H, J=7 Hz), 2.51 (s, 3H), 2.40–2.65 (m, 2H), 2.14 (s, 3H), 1.23–1.83 (m, 10H).

EXAMPLE 17

2-Acetpxymethyl-4-(7-phthalimidoheptyl)-6-methylpyridine (19)

Yield: 96% oil Rf=0.57 (System A) H¹NMR (60 MHz, CDCl$_3$): 7.61–7.96 (m, 4H), 7.06 (s, 2H), 3.39 (s, 2H), 3.67 (t, 2H, J=7 Hz), 2.51 (s, 3H), 2.42–2.67 (m, 2H), 2.20 (s, 3H), 1.23–1.83 (m, 10H).

EXAMPLE 18

2,6-Bisacetoxymethyl-4-(7-phthalimidoheptyl)-6-methylpyridine (20)

Yield: 80% oil Rf=0.71 (System A) H¹NMR (60 MHz, CDCl$_3$): 7.61–7.96 (m, 4H), 7.10 (s, 2H), 5.18 (s, 4H) 3.67 (t, 2H, J=7 Hz), 2.45–2.67 (m, 2H), 2.14 (s, 6H), 1.23–1.77 (m, 10H).

EXAMPLE 19

2,6-Bishydroxymethyl-4-(7-phthalimidoheptyl) pyridine (21)

Alkaline hydrolysis of phthalimido diester (20) gave as expected both the product with hydrolyzed ester functions only (21) and the by-product with an open phthalimido ring system. Both products were collected after short column purification since the latter is cyclizing back under conditions applied in the next step.
Total yield: 55% white crystals Rf=0.31 (System B) H¹NMR (60 MHz, CDCl$_3$) for pure (21): 7.61–7.96 (m, 4 H), 7.20 (s, 2 H), 5.35 (s, broad, 2 H), 4.50 (s, 4 H), 3.67 (t, 2 H, J=7 Hz), 2.45–2.67 (m, 2 H), 2.14 (s, 6 H), 1.23–1.77 (m, 10 H).

EXAMPLE 20

2,6-Bisbromomethyl-4-(7-phthalimidoheptyl) pyridine (22)

Yield: 78% white crystals Rf=0.73 (System A) H¹NMR (60 MHz, CDCl$_3$): 7.61–7.96 (m, 4 H), 7.28 (s, 2 H), 4.52 (s, 4 H), 3.67 (t, 2 H, J=7 Hz), 2.45–2.67 (m, 2 H), 2.14 (s, 6 H), 1.23–1.77 (m, 10 H).

EXAMPLE 21

4-(7-Phthalimidoheptyl)-2,6-bis(N,N-bis (ethoxycarbonylmethyl)-aminomethyl) pyridine (23)

Yield: 93% oil Rf=0.62 (System A) H¹NMR (400 MHz, CDCl$_3$): 8.06–8.08 (m, 2 H), 7.93–7.95 (m, 2 H), 7.51 (s, 2 H), 4.40 (q, 8 H, J=7.1 Hz), 4.23 (s, 4 H), 3.90 (t, 2 H, J=7.0 Hz), 3.83 (s, 8 H), 2.81 (t, J=7.6 Hz), 1.95-1.55 (m, 10 H), 1.49 (t, 12 H, J=7.1 Hz).

EXAMPLE 22

4-(7-Aminoheptyl)-2,6-bis(N,N-bis (ethoxycarbonylmethyl)aminomethyl)pyridine (24)

Compound (23) (400 mg, 0.55 mmol) was dissolved in dioxane (5 ml) and sodium hydroxide (2 M, 5 ml) was added. A mixture was stirred neutralized with conc. hydrochloric acid and evaporated almost to dryness. The residue was treated with hydrazine hydrate (2.0 ml) dissolved in ethanol (10 ml) and refluxed for 6 h. Volatile matter was evaporated and coevaporated with dry acetonitrile. The residue obtained was suspended in dry ethanol (50 ml) previously treated with thionyl chloride (4 ml). The mixture was refluxed for 2 h, filtered, evaporated and partitioned between saturated sodium hydrogen carbonate and chloroform. Combined chloroform extracts were dried over sodium sulphate, concentrated and finally purified using short column chromatography.
Yield: 232 mg (71%) oil Rf=0.15 (System B) H¹NMR (400 MHz, CDCl$_3$+CD$_3$OD): 7.29 (s, 2 H), 4.17 (q, 8 H, J=7 Hz), 4.00 (s, 4 H), 3.60 (s, 8 H), 2.72 (t, 2 H, 7.0 Hz), 2.58 (t, 2 H, J=7.3 Hz), 1.33–1.61 (m, 10 H), 1.26 (t, 12 H, J=7.0 Hz).

EXAMPLE 23

Hydrolysis of Compound (24) and Synthesis of Aminochelati (25)

Hydrolysis of compound (24) was performed analogously to Example 11. The product obtained was precipitated using standard acetone precipitation.

EXAMPLE 24

4-(3-Benzyloxypropyl)-2,6-dimethyl-pyridine (26)

A sodium amide solution in liquid ammonia was prepared from sodium (1.03 g, 44.6 mmol) in 100 ml of liquid ammonia according to Example 1.
Collidine (1), (5 g, 41.3 mmol) in dry tetrahydrofuran was added dropwise and the mixture was stirred for 60 min at −40° C. To this stirred mixture 1-benzoxy-2-bromethane (Tetrahedron Lett. 28, 2639–42, 1979) (8.24 g, 39.2 mmol) dissolved in dry tetrahydrofuran (20 ml) was added dropwise during 30 min and the reaction mixture was stirred overnight.
After evaporation of all volatile matter the residue was partitioned between sodium hydrogen carbonate and chloroform. Evaporation of the chloroform phase gave an oily residue which was distilled at reduced pressure—Sp. 145–150/12 mmHg.
Yield: 5.12 g (52%) oil Rf=0.58 (System A) H¹NMR (60 MHz, CDCl$_3$): 7.30 (s, 5 H), 6.73 (s, 2 H), 4.46 (s, 2 H), 3.43 (t, 2 H), 2.60 (t, 2 H), 2.42 (s, 6 H), 1.84 (m, 2 H).

EXAMPLES 25–31

From 4-(3-Benzyloxypropyl)-2,6-dimethylpyridine-N-oxide (27) to 4-(3-Benzyloxypropyl)-2,6-bis (N, N-bis(ethoxycarbonylmethyl)aminomethyl)pyridin e (33). Compounds 27–33 in Scheme 5

These compounds were prepared following the conditions from Examples 3, 4, 5, 6, 7, 8 and 9 respectively. Therefore, only the final results will be presented here.

EXAMPLE 25

4-(3-Benzyloxypropyl)-2,6-dimethylpyridine-N-oxide (27)

Yield: 90% oil Rf=0.42 (System A) H¹NMR (60 MHz, CDCl$_3$): 7.30 (s, 5 H), 6.91 (s, 2 H), 4.46 (s, 2 H),3.43 (t, 2 H), 2.60 (t, 2 H), 2.44 (s, 6 H), 1.84 (m, 2 H).

EXAMPLE 26

2-Acetoxymethyl-4-(3-benzyloxypropyl)-6-methylpyridine (28)

Yield: 70% oil Rf=0.64 (System A) H¹NMR (60 MHz, CDCl$_3$): 7.30 (s, 5 H), 6.95 (s, 1 H), 6.90 (s, 1 H), 5.11 (s, 2 H), 4.46 (s, 2 H), 3.46 (t, 2 H), 2.66 (t, 2 H), 2.46 (s, 3 H), 2.09 (s, 3 H), 1.86 (m, 2 H).

EXAMPLE 27

2-Acetoxymethyl-4-(3-benzyloxypropyl)-6-methylpyridine-N-oxide (29)

Yield: 97% oil Rf=0.5 (System A) H$^1$NMR (60 MHz, CDCl$_3$): 7.30 (n, 5 H), 7.03 (s, 2 H), 5.34 (s, 2 H), 4.46 (s, 2 H), 3.45 (t, 2 H), 2.68 (t 2 H), 2.46 (s, 3 H), 2.13 (s, 3 H), 1.86 (m, 2 H).

EXAMPLE 28

2,6-Bisacetoxymethyl-4-(3-benzyloxypropyl) pyridine (30)

Yield: 85% oil Rf=0.69 (System A) H$^1$NMR (60 MHz, CDCl$_3$): 7.30 (s, 5 H), 7.08 (s, 2 H), 5.14 (s, 4 H), 4.46 (s, 2 H), 3.45 (t, 2 H), 2.70 (t, 2 H), 2.09 (s, 6 H), 1.86 (m. 2 H).

EXAMPLE 29

2,6-Bishydroxymethyl-4-(3-benzyloxypropyl) pyridine (31)

Yield: 57% white crystals Rf=0.45 (System B) H$^1$NMR (60 MHz, CDCl$_3$): 7.31 (s, 5 H), 6.99 (s, 2 H), 4.68 (s, 4 H), 4.49 (s, 2 H), 3.69 (s, 2 H, exchangeable), 3.49 (t, 2 H), 2.74 (t, 2 H), 1.89 (m, 2 H).

EXAMPLE 30

2,6-Bisbromomethyl-4-(3-benzyloxypropyl)pyridine (32)

Yield: 54% oil Rf=0.70 (System C) H$^1$NMR (60 MHz, CDCl$_3$): 7.32 (s, 5 H), 7.14 (s, 2 H), 4.51 (s, 2 H), 4.48 (s, 4 H), 3.45 (t, 2 H), 2.71 (t, 2 H), 1.90 (m, 2 H).

EXAMPLE 31

4-(3-Benzyloxypropyl-2,6-bis(N,N-bis(ethoxycarbonylmethyl)-aminomethyl) pyridine (33)

Yield: 97% oil Rf=0.49 (System A) H$^1$NMR (60 MHz, CDCl$_3$): 7.30 (s, 5 H), 7.08 (s, 2 H), 4.46 (s, 2 H), 4.14 (q, 8 H), 3.95 (s, 4 H), 3.60 (s, 8 H), 3.43 (t, 2 H), 2.60 (t, 2 H), 1.90 (m, 2 H), 1.30 (t, 9 H).

EXAMPLE 32

4-(3-Hydroxypropyl)-2,6-bis(N,N-bis(ethoxycarbonylmethyl)aminomethyl) pyridine (34)

Compound (33) (520 mg, 0.83 mmol) and hydrobromic acid (5 ml, 47%) were refluxed together for 3 h. The homogeneous mixture was cooled and most of the acid was evaporated under reduced pressure.

The residue was dissolved in 20 ml of dry ethanol and refluxed for 2 h. This reesterified mixture was evaporated, dissolved in chloroform and the residual acid was extracted by sat. sodium hydrogen carbonate. The organic phase was evaporated and the title compound was purified by short column chromatography.

Yield: 376 mg (84%) oil Rf=0.32 (System A) H$^1$NMR (60 MHz, CDCl$_3$): 7.12 (s, 2 H), 4.14 (q, 8 H), 3.97 (s, 4 H), 3.45–3.60 (m, 10 H), 2.68 (t, 2 H), 1.86 (m, 2 H), 1.21 (t, 12 H).

EXAMPLE 33

Synthesis of Phosphodiester Derivative (35) of Compound (34)

Compound (34) (350 mg, 0.65 mmol) was coevaporated twice with dry pyridine, and dissolved in 10 ml of dry pyridine; then an o-chlorophenylphosphoro-bis-triazolide solution in dry acetonitrile (0.25 M, 6.0 ml, 1.5 mmol) was added. The mixture was stirred at RT for 60 min. Triethylammonium bicarbonate (10 ml, 1.3 M, pH 7.3) was added and the mixture was stirred for 5 min whereupon it was partitioned between sat. sodium hydrogen carbonate and chloroform.

The combined chloroform extracts (3×30 ml) were evaporated and the phosphodiester (35) purified by column chromatography using 20% MeOH/chloroform as eluent.

Yield: 460 mg (92%) oil Rf=0.51 (System D) H$^1$NMR (400 MHz, CDCl$_3$): 6.90–7.70 (m, 6 H), 4.15 (q, 8 H), 4.04 (t, 2 H), 3.98 (s, 4 H), 3.58 (s, 8 H), 3.06 (q, 6 H), 2.66 (t, 2 H), 1.92 (m, 2 H), 1.31 (t, 9 H), 1.24 (t, 12 H)

EXAMPLE 34

L-Lysine ethyl ester (36) in Scheme 6

Thionyl chloride (5.0 ml, 8.06 g, 68 mmol) was added dropwise to 500 ml of ice-cooled dry ethanol. The stirred mixture was kept for 20 min at this temperature and L-lysine hydrochloride (20 g, 109 mmol) was added.

The mixture was then refluxed for 3 h and concentrated to a volume of about 200 ml. 200 ml of diethylether was added and the crystallized product filtered off.

Yield: 29 g (97%)-dihydrochloride. Rf=0.20 (System F)

EXAMPLE 35

ω-N-(4-Nitrobenzoyl)-L-lysine ethyl ester (37)

L-lysine HCl (5 g, 27.4 mmol) dissolved in 50 ml of water was titrated with 5 M NaOH to pH 10.5. 4-Nitrobenzoyl chloride (6.6 g, 36 mmol) in dioxane (50 ml) and 5 M NaOH were slowly added keeping the vigorously stirred reaction mixture at pH 10.5.

After complete addition and disappearance of the pink colour the reaction mixture was acidified with conc. HCl to pH 2 and extracted four times with diethylether. The aqueous phase was concentrated to dryness, coevaporated twice with 200 ml of dry ethanol and suspended in 250 ml of dry ethanol previously treated with 10 ml of thionyl chloride. The mixture was refluxed for 3 h, filtered and evaporated. The residual material was partitioned between saturated sodium bicarbonate and chloroform/ethanol 1:1 and the organic phase was dried over magnesium sulfate yielding a crude product which was purified by flash chromatography using 5% EtOH/chloroform as eluent.

Yield: 1.08 g (12%) oil crystallizing on standing Rf=0.23 (System A) H$^1$NMR (60 MHz, CDCl$_3$): 8.25 (d, 2 H, J=9 Hz), 7.93 (d, 2 H, J=9 Hz), 6.87 (s, broad, 1 H), 3.99–4.34 (q, 2 H), 3.30–3.60 (m, 3 H), 1.40–1.75 (m, 8 H), 1.11–1.37 (t, 3 H)

EXAMPLE 36

α-N-(Methoxycarbonylmethyl)-ω-N-(4-nitrobenzoyl)-L-lysine ethyl ester (38)

Compound (37) (0.54 g, 1.7 mmol) was coevaporated with toluene, dissolved in dry acetonitrile (10 ml) and bromoacetic acid methylester (0.265 g, 1.7 mmol) was added followed by pulverized dry sodium carbonate (2.0 g). The mixture was refluxed for 3 h.

Filtration of the inorganic salts and evaporation of the acetonitrile gave an oily crude product which was purified by flash chromatography.

Yield: 0.45 g (68%) oil Rf=0.26 (System A) H$^1$NMR (60 MHz, CDCl$_3$): 8.25 (d, 2 H, j=9 Hz), 7.93 (d, 2 H, J=9 Hz), 6.63 (s, broad, 1 H), 3.95–4.30 (q, 2 H), 3.68 (s, 3 H), 3.30–3.60

EXAMPLE 37

ω-N-Monomethoxytrityl-L-lysine ethyl ester (39)

Dry triethylamine (1.8 ml, 18 mmol) was added to a suspension of (36) (1.5 g, 6 mmol) in 20 ml of dry pyridine. To this mixture stirred at RT, solid monomethoxytrityl chloride (1.96 g, 6 mmol) (MMTrCl) was added in small portions during a period of 1 h whereupon the mixture was stirred for additional 2 h. A standard sodium bicarbonate work-up, followed by extraction with chloroform, yielded a crude product contaminated with α-MMTr isomer.

The pure title product was easily isolated by flash column chromatography due to the large Rf difference between the isomers.

Yield: 1.35 g (48%) oil Rf=0.43 (System A) H$^1$NMR (400 MHz, CDCl$_3$): 7.5-6.75 (m, 14 H), 4.18-4.13 (q, 2 H), 3.78 (s, 3 H), 3.45-3.37 (m, 1 H), 2.14-2.10 (t, 2 H, J=7 Hz), 1.75-1.35 (m, 9 H), 1.26 (t, 3 H)

EXAMPLE 38

α-N-(Methoxycarbonylmethyl)-ω-N-monomethoxytrityl-L-lysine ethyl ester (40)

A partially protected L-lysine derivative (39) (1.0 g. 2.13 mmol) was converted to product (40) using the method described in Example 36.

Yield: 0.81 g (70%) oil Rf=0.73 (System A) H$^1$NMR (400 MHz, CDCl$_3$): 7.46-6.77 (m, 14 H), 4.19-4.14 (q, 2 H), 3.77 (s, 3 H), 3.70 (s, 3 H), 3.31–3.45 (q, 2 H), 3.22–3.25 (t, 1 H), 2.09–2.12 (t, 2 H), 1.35–1.70 (m, 6 H), 1.23–1.27 (t, 3 H)

EXAMPLE 39

ω-N-Trifluoroacetyl-L-lysine ethyl ester (41)

Compound (36) (2.0 g, 8.1 mmol) dissolved in 10 ml of dry ethanol was treated with dry triethylamine (4.09 g, 40.4 mmol). Ethyl trifluoroacetate (1.5 g, 10.5 mmol) was added to the stirred suspension formed, and the mixture was refluxed for 6 h.

All volatiles were then evaporated and the residue was partitioned between saturated sodium hydrogen carbonate and chloroform/ethanol 1:1.

The combined organic phase (5×60 ml) was evaporated, coevaporated with toluene and flash chromatography to give title product in the form of a colorless oil.

Yield: 1.9 g (87%) Rf=0.72 (System D) H$^1$NMR (400 MHz, CDCl$_3$): 7.10 (t, 1 H, exchangeable), 4.21-4.16 (q, 2 H), 3.45-3.40 (m, 1 H), 3.38-3.31 (m, 2 H), 1.84 (s, 2 H, exchangeable), 1.82-1.40 (m, 6 H), 1.28 (t, 3 H).

EXAMPLE 40

α-N-(Methoxycarbonylmethyl)-ω-N-trifluoroacetyl-L-lysine ethyl ester (42)

L-lysine derivative (41) (1.0 g, 3.7 mmol) was converted to the product (42) by means of a method analogous to Example 36.

Yield: 1.05 g (83%) oil Rf=0.48 (System A) H$^1$NMR (60 MHz, CDCl$_3$+CD$_3$OD): 4.4-4.0 (q, 2 H), 3.68 (s, 3 H), 3.5-3.1 (m, 5 H), 1.8-1.4 (m, 6 H), 1.23 (t, 3 H).

EXAMPLE 41

ω-N-(4-Hydroxybutyryl)-L-Lysine ethyl ester (43)

L-lysine ethyl ester × 2 HCl (36) (2 g, 8.1 mmol) in 30 ml of dry ethanol was treated with dry triethylamine (5.63 ml, 40.5 mmol) and γ-butyrolactone (0.7 g, 8.1 mmol) and the resultant suspension was refluxed for 3 h.

Evaporation of volatiles and coevaporation with toluene yielded a crude product which was purified by flash chromatography using 20% methanol/chloroform as solvent.

Yield: 1.54 g (73%) oil Rf=0.28 (System D) 1 H$^1$NMR (400 MHz, CDCl$_3$+CD$_3$OD): 4.30-4.22 (q, 2 H), 3.72–3.77 (m, 1 H), 3.58–3.65 (t, 2 H), 3.18–3.28 (m, 2 H), 2.30–2.36 (t, 2 H), 1.40–2.00 (m, 8 H), 1.28–1.34 (t, 3 H).

EXAMPLE 42

α-N-(methoxycarbonylmethyl)-ω-N-(4-hydroxybutyryl)-L-lysine ethyl ester (44)

Compound (43) (1.22 g, 4.68 mmol) in 20 ml of dry acetonitrile was converted to product (44) in a reaction analogous to that in Example 36.

Yield: 1.04 g (64%) oil Rf=0.18 (System A) H$^1$NMR (400 MHz, CDCl$_3$): 6.25 (s, broad, 1 H), 4.16–4.21 (q, 2 H), 3.73 (s, 3 H), 3.67–3.69 (t, 2 H), 3.33–3.49 (m, 2 H), 3.20–3.30 (m, 3 H), 2.34–2.47 (t, 2 H), 1.40–1.90 (m, 8 H), 1.26–1.30 (t, 3 H).

EXAMPLE 43

2-(N,N-Bis(ethoxycarbonylmethyl)aminomethyl-6-(N-methoxy carbonylmethyl-N-(5-N-(4-nitrobenzoyl)-1-ethoxycarbonyl aminopentyl)) aminomethyl pyridine (47)

Step A:

2,6-Bisbromomethyl pyridine (241 mg, 0.91 mmol) in dry acetonitrile (10 ml) was reacted with compound (38) (360 mg, 0.91 mmol) in the presence of 2 g pulverized dry sodium carbonate at RT with vigorous stirring. The resulting mixture composed of unreacted pyridine derivative, monobromodiester (45) (Rf=0.72 in System A) and tetraester (46) (Rf= 0.47 in System A) was evaporated, coevaporated with toluene and flash chromatographed to obtain pure (45) in a 52% yield—oil.

H$^1$NMR (400 MHz, CDCl$_3$): 8.23 (d, 2 H, J=8.5 Hz), 8.00 (d, 2 H, J=8.5 Hz), 7.25–7.55 (m, 3 H), 6.83 (s, 1 H, broad), 4.49 (s, 2 H), 4.15–4.23 (q, 4 H), 3.91–4.06 (dd, 2 H, J=5 Hz), 3.54–3.69 (dd, 2 H, J=8 Hz), 3.63 (s, 3 H), 3.42–3.52 (m, 3 H), 1.50–1.95 (m, 6 H), 1.30 (t, 3 H).

Continuation of this chromatographic purification resulted in isolation of symmetrical tetraester (46) in an 18% yield—oil.

H$^1$NMR (400 MHz, CDCl$_3$): 8.24 (d, 4 H, J=9 Hz), 8.01 (d, 4 H, J=9 Hz), 7.37 (s, 3 H), 6.94 (t, 2 H, broad), 4.16 (q, 4 H, J=6.1 Hz), 3.94 (dd, 4 H, J=15 Hz), 3.58 (d, d, 4 H, J=17.7 Hz), 3.63 (s, 6 H), 3.38–3.50 (m. 6 H). 1.50–1.80 (m. 12 H. 1.28

Step B:

Compound (45) (100 mg, 0.17 mmol) was coevaporated with dry acetonitrile, dissolved in 3 ml of acetonitrile, and 1 g of dry pulverized sodium carbonate was added followed by iminoacetic acid diethyl ester (36 mg, 0.19 mmol). The mixture was refluxed overnight, filtered and evaporated.

The residue was chromatographed yielding pure title compound (47).

Yield: 92% oil Rf=0.57 (System A) H$^1$NMR (400 MHz, CDCl$_3$): 8.25 (d, 2 H, J=7 Hz), 8.02 (d, 2 H, J=7 Hz), 7.40–7.55 (m, 3 H), 6.91 (t, 1 H, broad), 4.12–4.22 (m, 6 H), 3.89–4.04 (dd, 2 H, J=15 Hz), 4.00 (s, 2 H), 3.52–3.68 (dd, 2 H, J=17.5 Hz), 3.63 (s, 3 H), 3.59 (s, 4 H), 3.40–3.50 (m, 3 H), 1.50–1.80 (m, 6 H), 1.20–1.30 (m, 9 H).

EXAMPLE 44

2-(N,N-Bis(ethoxycarbonylmethyl))aminomethyl-6-(N-methoxycarbonylmethyl-N-(5-N-(4-aminobenzoyl)-1-ethoxycarbonylaminopentyl)) aminomethyl pyridine (48)

Solid sodium borohydride (11.3 mg, 0.3 mmol) was added to a mixture of compound (47) (100 mg, 0.15 mmol) and 2 g of palladium on carbon (10%) in 5 ml of dry ethanol. The mixture was stirred at RT for 10 min and partitioned between saturated sodium hydrogen carbonate and chloroform. Evaporated organic extracts were flash chromatographed yielding (48) in the form of an oil.

Yield: 89% Rf=0.37 (System A) H$^1$NMR (400 MHz, CDCl$_3$): 7.63 (d, 2 H, J=8.7 Hz), 7.38–7.55 (m, 3 H), 6.64 (d, 2 H, J=8.7 Hz), 6.28 (t, 1 H, broad), 4.12–4.20 (m, 6 H), 3.89–4.05 (dd, 2 H, J=15.2 Hz), 4.01 (s, 2 H), 3.70 (s, 3 H), 3.64 (s, 4 H), 3.50–3.67 (dd, 2 H, J=17.7 Hz), 1.45–1.80 (m, 6 H), 1.20–1.30 (m, 6 H).

EXAMPLE 45

Hydrolysis of Compound (48), Formation of Europium Chelate and Its Conversion to the Isothiocyanate (49)

This standard cycle of reactions has been made following the general prescriptions of Example 12.

The product was characterized on the basis of a) IR spectroscopy—the presence of isothiocyanate vibration at 2070 cm$^{-1}$ b) Thin layer chromatography using acetonitrile/water (4:1) as the solvent—single spot with Rf=0.28 showing positive (UV-360 nm) test for europium$^{3+}$ after spraying with an ethanolic solution of 2-naphthoyltrifluoroacetone (2-NTA) and negative test for free amino group—spraying with fluoram.

c) HPLC chromatography—using ion exchanging Ultrapac Column—TSK DEAE-5PW (LKB). Running conditions: Triethylammonium bicarbonate buffer, pH 7.3, linear gradient 0.01→0.60 M in 30 min. Flow rate 1.2 ml/min and detection at 278 nm.

EXAMPLE 46

2-(N,N-Bis(ethoxycarbonylmethyl)aminomethyl-6-(N-methoxycarbonylmethyl-N-(5-N- trifluoroacetyl-1-ethoxycarbonylaminopentyl)) aminomethyl pyridine (50)

This product has been synthesized following the two-stage procedure of Example 43, and using compound (42) as a substrate in step A. The final chromatographic separation yielded the desired product as a colourless oil in a 45% overall yield (based on starting 2,6-dibromomethyl pyridine).

Rf=0.48 (System A)

H$^1$NMR (400 MHz, CDCl$_3$): 7.64 (t, 1 H, J=7.7 Hz), 7.45 (d, 1 H, J=7.7 Hz), 7.42 (d, 1 H, J=7.7 Hz), 7.15 (s, 1 H, broad), 4.13–4.22 (m, 6 H), 4.03 (s, 2 H), 3.88–4.04 (dd, 2 H, J=15 Hz), 3.66 (s, 3 H), 3.61 (s, 4 H), 3.48–3.68 (dd, 2 H, J=17.8 Hz), 3.33–3.45 (m, 3 H), 1.50–1.80 (m, 6 H), 1.20–1.32 (m, 9 H).

EXAMPLE 47

Hydrolysis of Compound (50), Formation of Europium Chelate and Its Conversion to the Bromoacetamido Derivative (51)

Hydrolysis of compound (50) (0.75 g, 1.14 mmol), and its chelate formation have been performed according to the general descriptions from Example 12.

To the water solution of this europium chelate N-ethyl-N,N-diisopropylamine (0.29 g, 2.24 mmol) was added, followed by bromoacetylchloride (0.54 g, 3.43 mmol) dissolved in 10 ml chloroform. The solution was stirred for 15 min. The chloroform phase was separated and the water phase was neutralized with sodium bicarbonate. The desired product (51) was obtained in the form of a white powder after concentration of the water phase and precipitation with acetone.

EXAMPLE 48

2-(N,N-Bis(ethoxycarbonylmethyl))aminomethyl-6-(N-methoxycarbonylmethyl-N-(5-N-(4-hydroxybutyryl)-1-ethoxycarbonylaminopentyl))-aminomethyl pyridine (52)

This product has been synthesized following the two-stage procedure of Example 43 and using compound (44) as a substrate in step A.

Yield: 56% oil Rf=0.25 (System A) H$^1$NMR (400 MHz, CDCl$_3$+CD$_3$OD): 7.66 (t, 1 H, J=7.6 Hz), 7.47 (d, 2 H, J=7.6 Hz), 6.28 (s, broad, 1 H), 4.17 (q, 6 H, J=7.0 Hz), 4.03 (s, 2 H), 3.96 (dd, 2 H, J=15.1 Hz), 3.70 (t, 2 H, J=7.0 Hz), 3.67 (s, 3 H), 3.61 (s, 4 H), 3.59 (dd, 2 H, J=17.3 Hz), 3.43 (t, 1 H, J=5.6 Hz), 3.23 (m, 2 H), 2.36 (t, 2 H, J=6.8 Hz), 1.86 (m, 2 H), 1.72 (m, 2 H), 1.38–1.60 (m, 4 H), 1.29 (t, 3 H), 1.27 (t, 6 H).

EXAMPLE 49

Synthesis of Phosphoramidate Derivative (53) of Compound (52)

To compound (52) (0.52 g, 1 mmol) dissolved in anhydrous dichloromethane (10 ml) was added diisopropylethylamine (0.78 ml, 4.6 mmol) followed by 2-cyanoethyl-N,N-diisopropylaminophosphochloridate (0.47 g, 2 mmol).

After 15 min stirring at RT the mixture was washed with cold sodium bicarbonate, extracted with dichloromethane, evaporated and purified by silica gel column chromatography using petroleum ether/triethylamine 9:1 as eluting solvent.

Yield: 85% (colourless oil Rf=0.42 (System A) P$^{31}$NMR (400 MHz, CDCl$_3$): 148.5 ppm. singlet (reference 85% phosphoric acid)

EXAMPLE 50

Coupling of compound 49 to swine IgG

An IgG fraction of swine-anti-mouse IgG was labeled with Eu$^{3+}$ by using different bifunctional chelating agents. The reagents used were p-isothiocyanatophenyl-EDTA synthesized according to Sundberg et al. (J.Med.Chem. 1974; 17, 1304–7), the N-1 and N-2 derivatives of p-isothiocyanatobenzyl-DTTA accoridng to Mikola et al. (EP-A-139675) and the pyridine derivative (49) as described above. 1 mg of IgG was incubated in 50 mM of carbonate buffer, pH 9.8, with a 50-fold molar excess of isothiocyanate-activated labeling reagents at +4° C. overnight. The labeled IgG was separated from free reagents by gel filtration through a Sephadex G50 column, and the labeling degree (Eu/IgG) was calculated by measuring the $Eu^{3+}$ by fluorometry (HemmilX et al., Anal.Biochem. 1984; 137, 335–43). The bromoacetyl activated chelates were coupled to IgG in similar conditions with the exception that coupling was allowed to proceed at room temperature overnight.

EXAMPLE 51

The stability of the chelates and their IgG conjugates was tested and compared to DTTA-Eu conjugates (EP-A-139, 675) in different conditions.

1. The release of $Eu^{3+}$ from compound (12) was warmed at 98° C. In spite of a small fraction released in the beginning, the chelate remained unchanged (Table 1).

TABLE 1

| Inc. time (min.) | Total $Eu^{3+}$ (pM) | Free $Eu^{3+}$ (pM) | Free $Eu^{3+}$ % |
|---|---|---|---|
| 0 | 630 | 42 | 6.7 |
| 5 | 658 | 67 | 10.1 |
| 15 | 684 | 89 | 13.0 |
| 30 | 691 | 104 | 15.0 |
| 50 | 704 | 118 | 16.7 |

TABLE 1-continued

| Inc. time (min.) | Total $Eu^{3+}$ (pM) | Free $Eu^{3+}$ (pM) | Free $Eu^{3+}$ % |
|---|---|---|---|
| 90 | 703 | 111 | 15.8 |
| 140 | 720 | 115 | 14.8 |

2. The compound 13 and its IgG conjugate were tested in acrylamide gel electrophoresis by using 1500 V, 60° C. in buffer containing 10 mM EDTA. Compounds used for comparision were the N-1 and N-2 derivatives of p-isothiocyanatobenzyl-DTTA-$Eu^{3+}$ and their IgG conjugates. In these conditions the N-1-DTTA-Eu dissociated $Eu^{3+}$ totally, the N-2 derivative by 20% and the pyridine derivative (compound 13) dissociated none of its $Eu^{3+}$.

3. The stabilities of the labeled IgGs (Example 50) were followed upon storage in a buffer containing 0.1 mM EDTA, at 37° C. The remaining $Eu^{3+}$ was assayed daily by means of immunobinding to MIgG-coated microtitration strips. The results are presented in FIG. 1.

FIG. 1: The retained $Eu^{3+}$ on labeled anti-mouse IgG after storage at 37° C. in a buffer containing 0.1 mM EDTA. The symbols represent phenyl-EDTA-Eu (3), N-1-benzyl-DTTA-EU (Δ), N-2-benzyl-DTTA-Eu (o), and a pyridine derivative according to the invention (compound 49).

Scheme 1.

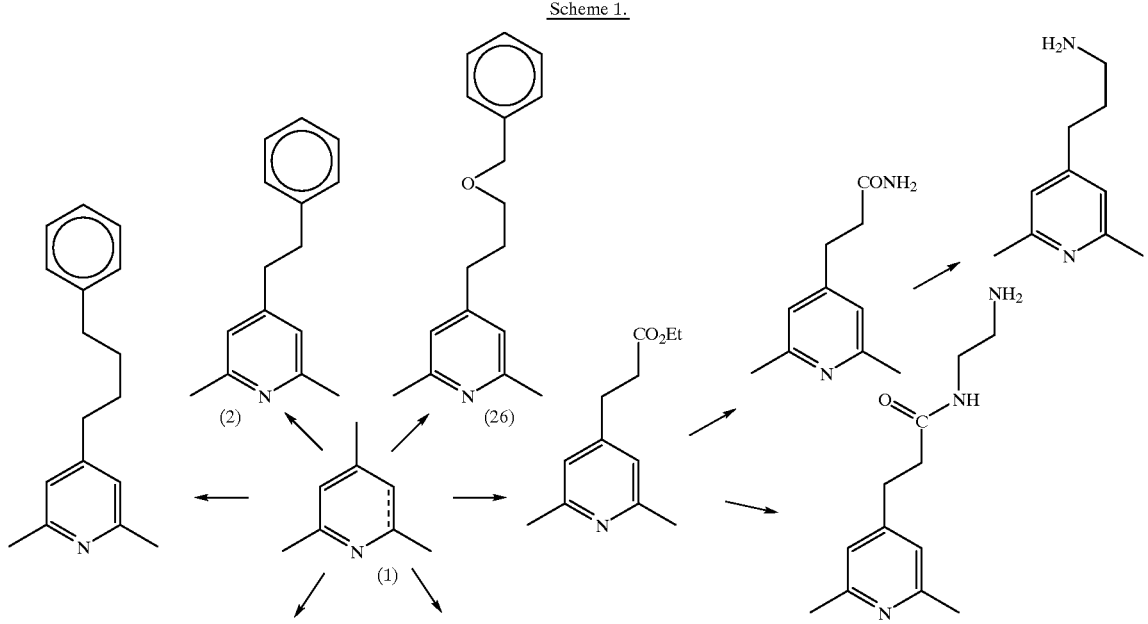

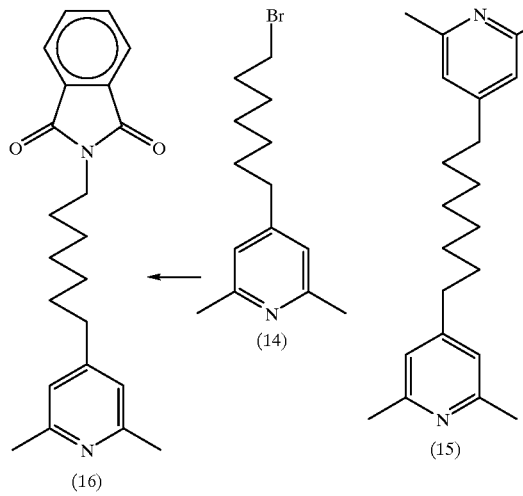
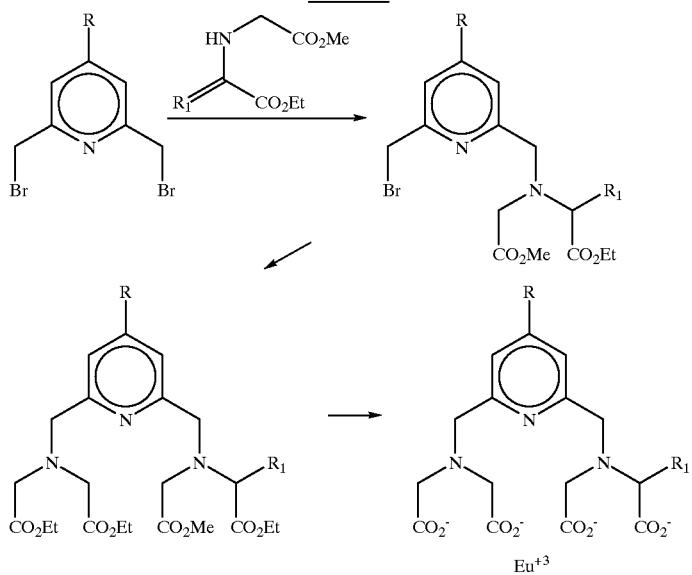
Scheme 2.
$R_1$ A protected side chain of any multifunctional α-aminoacid
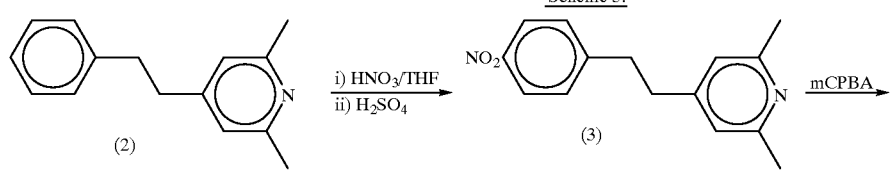
Scheme 3.

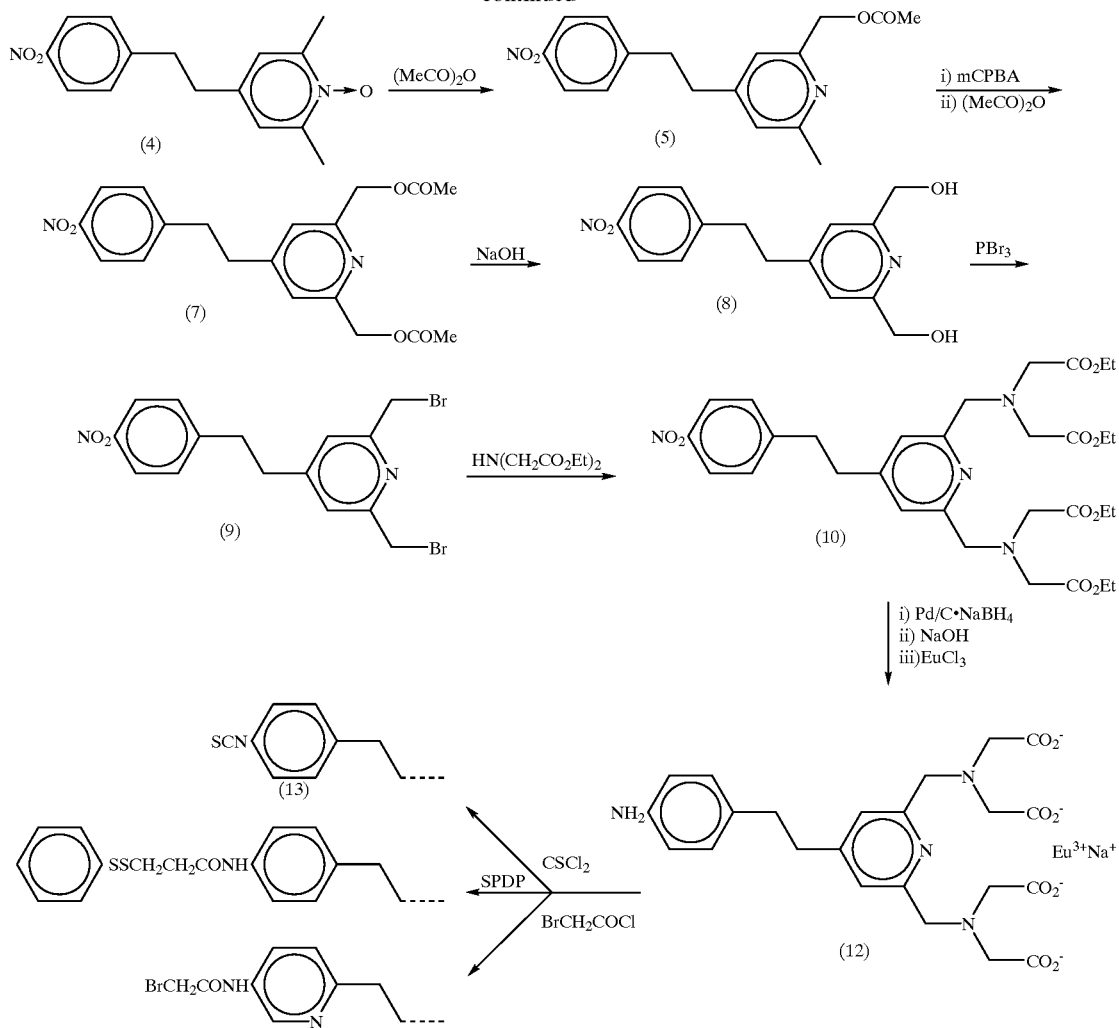
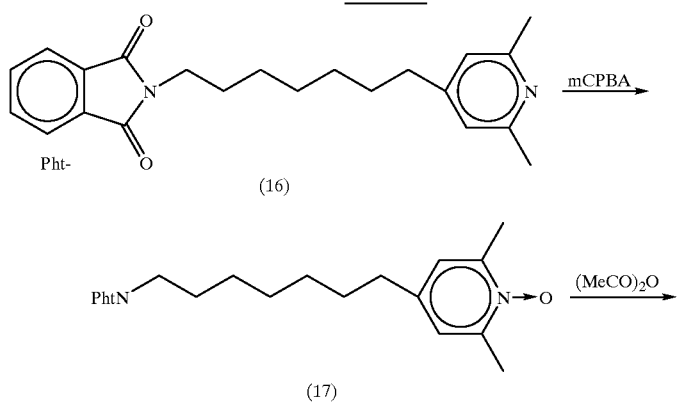
Scheme 4.

-continued
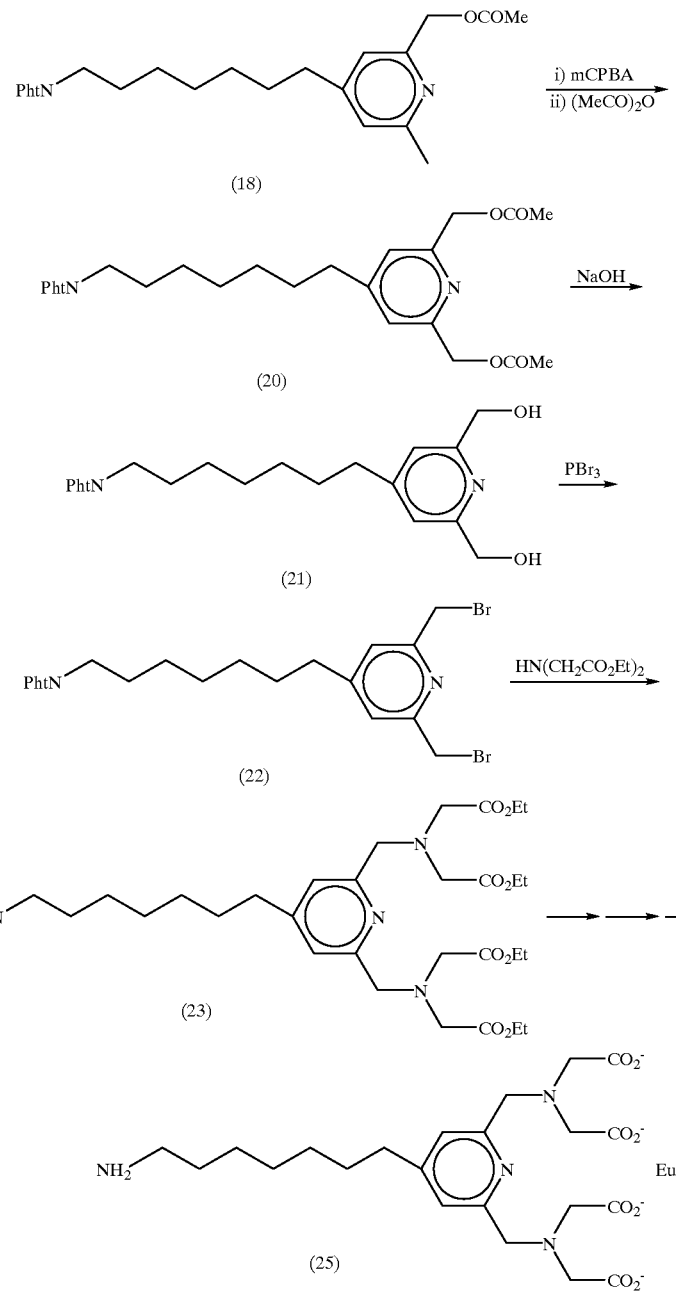

Scheme 5.
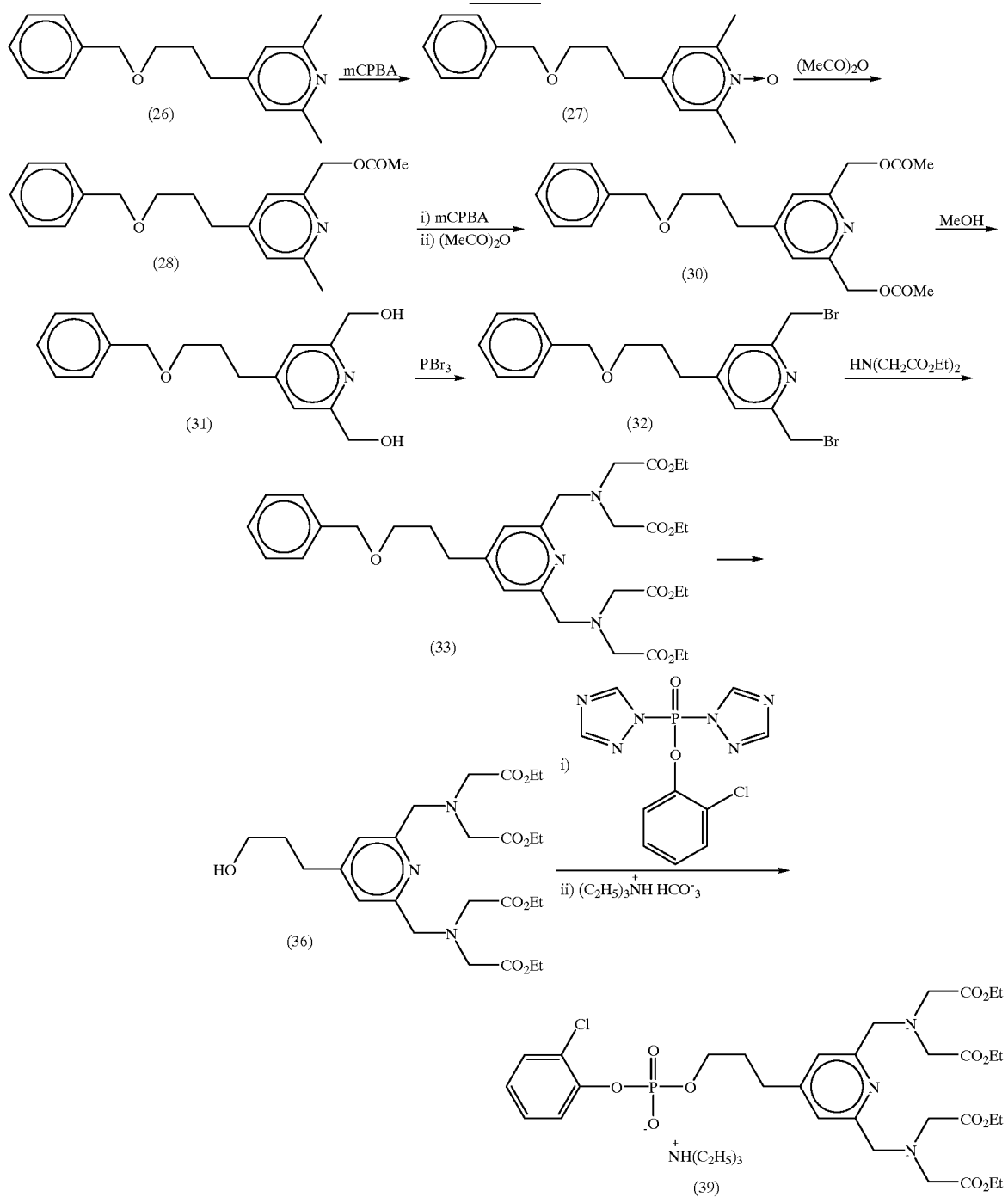

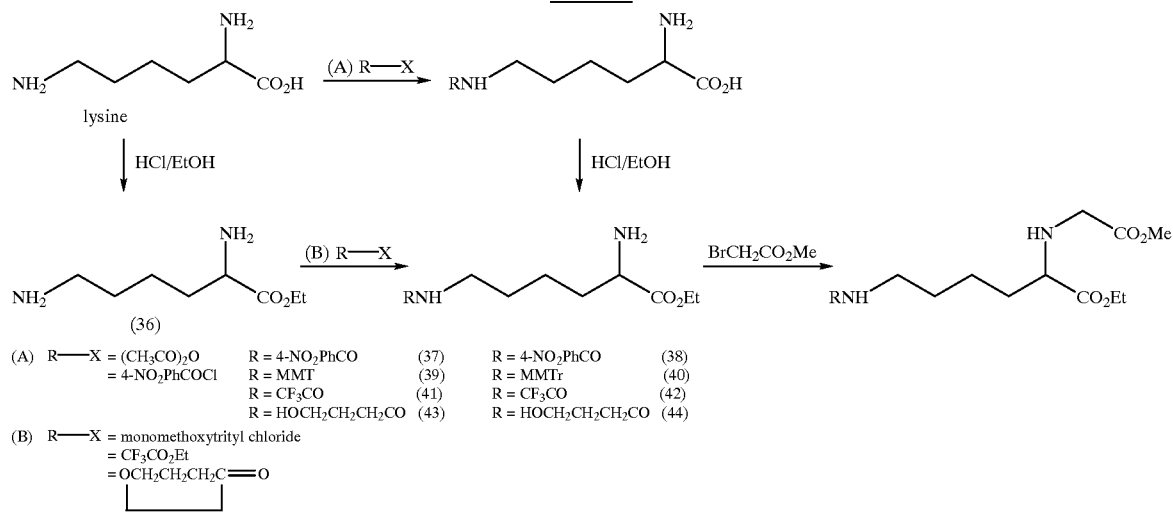
Scheme 6.

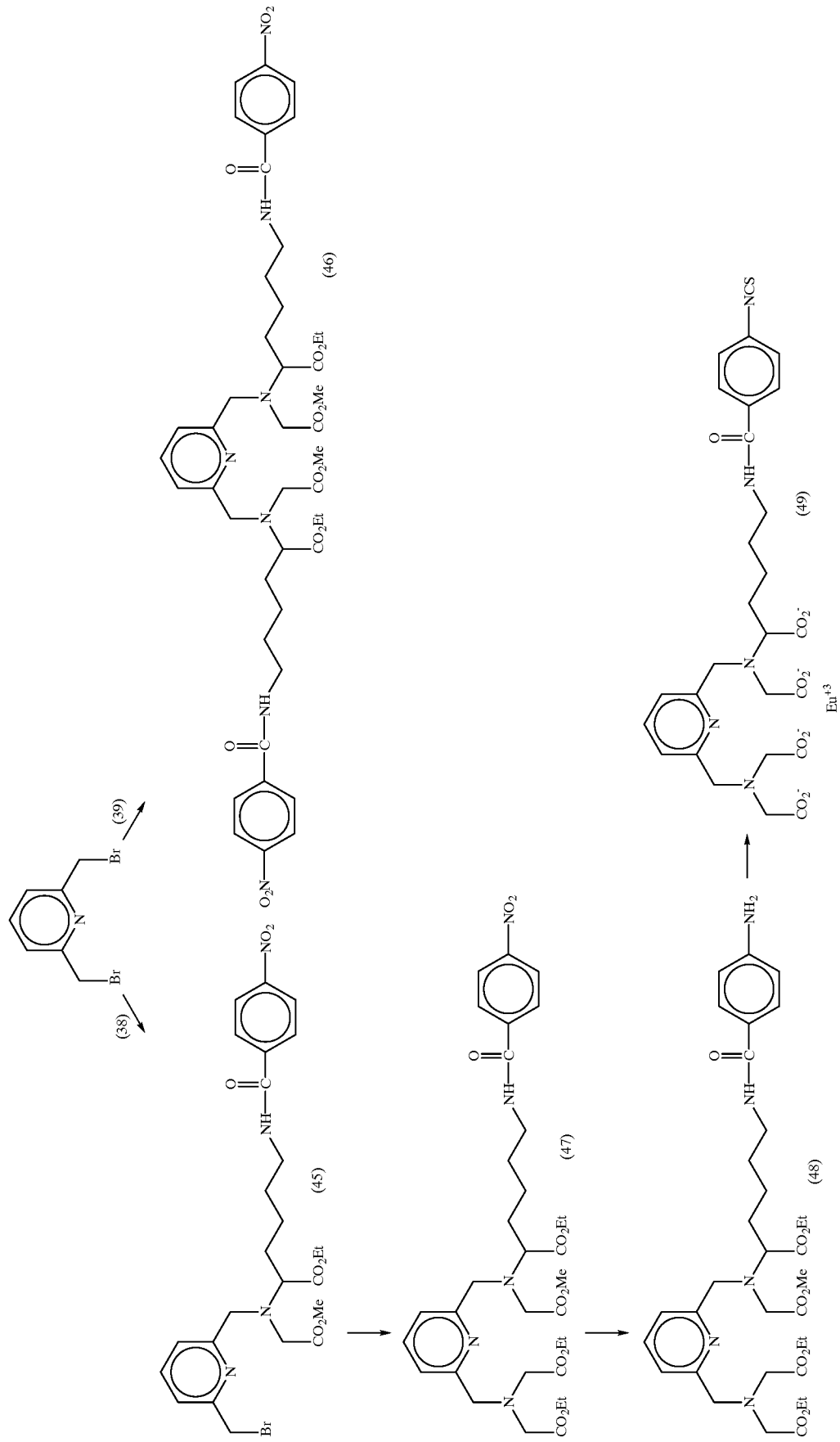

Scheme 8.

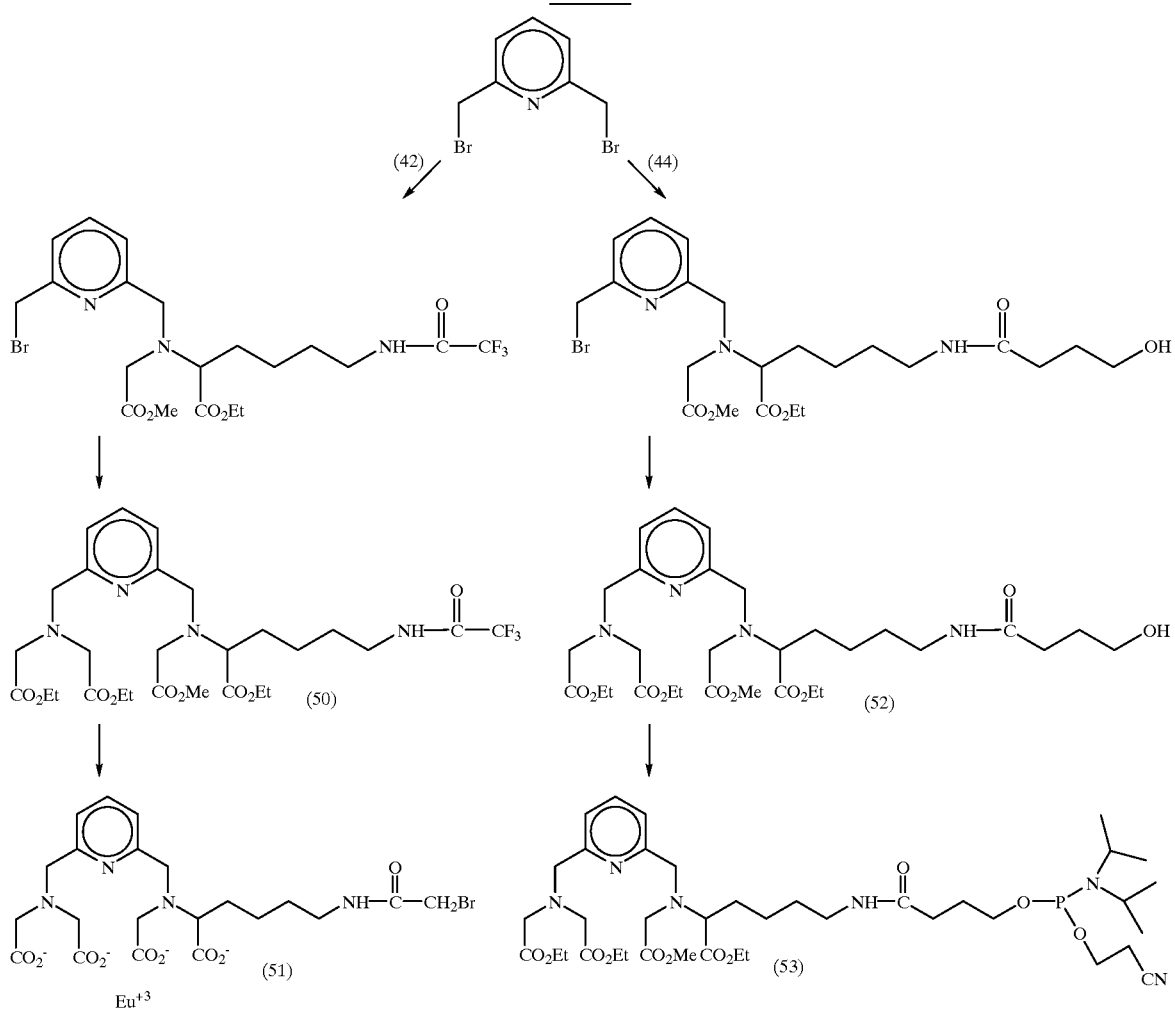

We claim:
1. A bifuncitonal chelating 2,6-disubstituted pyridine compound having the structure

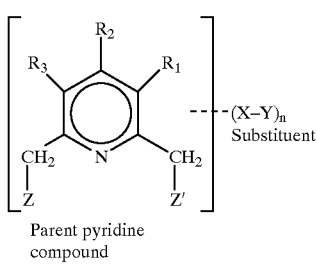

Parent pyridine compound where
(i) n is an integer 1 or 2
(ii) $R_1$, $R_2$ and $R_3$ represent hydrogen, or alkyl or aralkyl groups having 1–12 carbon atoms and have an aliphatic carbon atom next to the pyridine ring and no electrons capable of delocalizing or resonating with the pyridine ring, at least two of $R_1$, $R_2$ and $R_3$ being hydrogen;
(iii) Z and Z' represent identical or different chelating structures, in which the chelating h eteroatom is selected from amino nitrogens and negatively charged oxygens having a free pair of electorns so that the said at least one chelating heteroatom together with the nitrogen of the pyridine ring is capable of chelating a metal ion: the bridge linking two chelating heteroatoms together providing a distance of two or three atoms between them;
(iv) - - - indicates that the group X-Y is a substituent replacing one of the groups $R_1$, $R_2$ and $R_3$ or replacing a hydrogen atom in the Z and/or Z' groups,
(v) X-Y represents an organic group which is inert towards said chelating and which has no heteroatom closer than four atoms from a chelating heteroatom in Z or Z' and in which X is an inert and stable bridge and Y is
   (1) a funcitonal group selected for bromoacetamido, iodoacetamido, succinamido, pyridyldithio, mercapto, carboxyl, carboxylic ester of N-hydroxysuccinimide, p-nitrophenyl carboxylic ester, hydroxyl, aldehyde, diazonium, tosyl, mesytylyl, trexyl, phosphodiester and phosphotriester; or
   (2) a residue of a targeting compound participating in biospecific affinity reaction and with retained capability of participating in such reactions, said group X-Y being linked to the pyridine ring of formula II via an aliphatic carbon atom attached to said ring and providing no pi-electron system directly conjugated to said ring; or acid, ester salt and chelate forms thereof associated with at least one of said chelating heteroatoms.

2. A bifunctional chelating 2,6-disubstituted pyridine compound having the structure

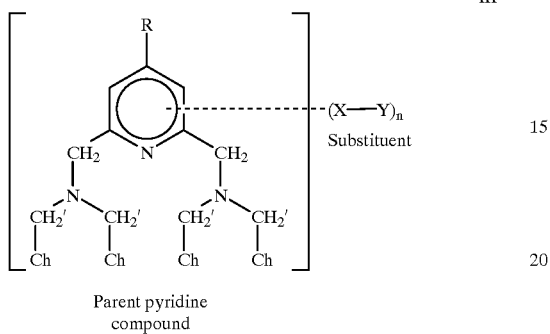

III

Parent pyridine compound where
(i) n is an integer 1 or 2;
(ii) $R_2$ represents alkyl and aralkyl groups of 1–12 carbon atoms that have an aliphatic carbon atom next to the pyridine ring and no electrons capable of delocalizing or resonating with the pyridine ring;
(iii) Ch represents chelating groups selected from —COO⁻, —PO$_3{}^2$ and —O—PO$_3{}^{2-}$;
(iv) - - - indicates that the group X-Y is a substituent replacing $R_2$ or a hydrogen atom H', with the provision that n always is 1 when $R_2$ is replaced;
(v) X-Y represents an organic group which is inert towards said chelating groups by having no chelating heteroatom closer than four atoms from a chelating heteroatom in Ch and
  (a) in which X is a stable bridge consisting of structural elements selected from —NR— (secondary or tertiary amino), —CONR— and —NRCO— (substituted amide), —S—S—(aliphatic disulfide), —S— (aliphatic thioether), —O— (ether), —COO— and —OOC— (ester), —N═N— (diaza) and pure hydrocarbon chains of 1–12 carbon atoms, in which elements R is selected from hydrogen and alkyl having less than 5 carbon atoms, and
  (b) in which Y is selected from
    (1) residue of a targeting compound participating in biospecific affinity reacitons in with retained capability of participating in such reactions, and
    (2) functional group selected from bromoacetamido, iodoacetamido, succinamido, pyridyldithio, mercapto, carboxyl, carboxylic ester with N-hydroxysuccinimide, p-nitrophenyl, carboxylic ester, hydroxyl, aldehyde, diazonium, tosyl, mesytylyl, trexyl, phosphodiester and phosphotriester; and
  (c) said group X-Y being linked to the pyridine ring of formula II via an aliphatic carbon atom attached to said ring and providing no pi-electron system directly conjugated to said ring;
or acid, ester, salt and chelate forms thereof associated with at least one of said chelating heteroatoms of Z.

* * * * *

UNITED STATES PATENT AND TRADEMARK OFFICE
CERTIFICATE OF CORRECTION

PATENT NO.   : 6,127,529
DATED        : October 3, 2000
INVENTOR(S)  : Marek Kwiatkowski, et al.

It is certified that error appears in the above-identified patent and that said Letters Patent is hereby corrected as shown below:

Column 34, claim 1,
Line 66, change "reaction" to -- reactions --;

Column 35, claim 1,
Line 4, after "ester", insert -- , --;

Column 35, claim 2,
Line 33, before "and", change "$PO_3^{2}$" to -- $PO_3^{2-}$ --;
In the formula, line 11, change "R" to -- $R_2$ --;

Column 36, claim 2,
Line 27, change "II" to -- III --.

Signed and Sealed this

Sixth Day of November, 2001

Attest:

*Nicholas P. Godici*

NICHOLAS P. GODICI
*Attesting Officer*   *Acting Director of the United States Patent and Trademark Office*